United States Patent [19]

Tien

[11] 4,007,435
[45] Feb. 8, 1977

[54] SENSOR DEVICE AND METHOD OF MANUFACTURING SAME

[76] Inventor: Tseng-Ying Tien, 660 Archwood Drive, Ann Arbor, Mich. 48103

[22] Filed: Apr. 25, 1974

[21] Appl. No.: 464,019

Related U.S. Application Data

[63] Continuation-in-part of Ser. No. 384,029, July 30, 1973, abandoned.

[52] U.S. Cl. .................................. 338/34; 73/23
[51] Int. Cl.² .................................... G01N 27/12
[58] Field of Search ............. 73/27 R, 23, 362 AR, 73/362 SC; 338/28, 34, 36; 324/715 N, 65 R; 23/254 E; 340/237 R; 200/85 A

[56] References Cited

UNITED STATES PATENTS

| | | | |
|---|---|---|---|
| 2,445,073 | 7/1948 | Marette et al. | 338/34 |
| 3,019,404 | 1/1962 | Fastenau et al. | 338/28 |
| 3,188,594 | 6/1965 | Koller et al. | 338/28 |
| 3,271,719 | 9/1966 | Ovshinsky | 338/34 |
| 3,611,243 | 10/1971 | Hardtl | 338/34 |
| 3,695,848 | 10/1972 | Taguchi | 73/27 R X |
| 3,699,803 | 10/1972 | Sumi | 73/27 R |
| 3,742,419 | 6/1973 | Martzloff | 73/362 SC X |

OTHER PUBLICATIONS

Seiyama et al., "Study on a Detector for Gaseous Components Using Semiconductive Thin Films", Analytical Chemistry, vol. 38, No. 8, July 1966, pp. 1069-1073.

*Primary Examiner*—Richard C. Queisser
*Assistant Examiner*—Stephen A. Kreitman
*Attorney, Agent, or Firm*—Reising, Ethington, Barnard, Perry & Brooks

[57] ABSTRACT

An oxygen sensing device particularly suited as a sensor for the exhaust gases of internal combustion engines, the sensing device comprising an electrically insulative ceramic element having bonded on the surface thereof a layer of an oxygen sensing metal oxide, preferably titania, and a pair of electrical leads for the oxygen sensing metal oxide, the device also having a layer of electrical resistance heating material adjacent to the layer of oxygen sensing metal oxide but separated therefrom by a layer of the electrically insulative ceramic, a pair of electrical leads for the electrical resistance heating material, and a layer of ceramic covering the layer of electrical resistance heating material.

20 Claims, 4 Drawing Figures

SENSOR DEVICE AND METHOD OF MANUFACTURING SAME

This application is a continuation-in-part of U.S. patent application Ser. No. 384,029, filed July 30, 1973, now abandoned.

FIELD OF THE INVENTION

The subject matter of the present invention is an oxygen sensing device, and method for manufacturing same, particularly suited for use as a sensor for internal combustion engine exhaust gases to determine the air/fuel ratio or to determine, in the case of exhaust emissions, the oxygen/unburned or partially burned hydrocarbon ratio.

BACKGROUND OF THE INVENTION

It has long been known that the electrical resistivity at a given temperature of any of a number of metal oxides is a function of the partial pressure of oxygen in the gaseous atmosphere or environment to which the metal oxide is exposed. Among the metal oxides having this characteristic are the transition metal oxides such as titanium dioxide, vanadium oxide, chromium oxide, manganese oxide, cobalt oxide, nickel oxide, iron oxide, and rare earth oxides an example of which is cerium oxide. This characteristic of such oxides has led to the suggestion of using same as a sensor element to determine the composition of internal combustion engine exhaust gases. Such systems, as well known in the prior art, comprise the sensor element, formed of a body of the metal oxide, located in the exhaust gas stream and having connected thereto a pair of electrical leads suitable connected, in spaced relationship to each other, to a relationship to oxide body for measuring the electrical resistance of the sensing metal oxide between the two leads. The information so gathered, concerning the composition of the exhaust gases and hence the proportion of unburned or only partially burned hydrocarbon therein, can be fed to a suitable circuit and control mechanism to control the air/fuel ratio of the mixture fed into the combustion chamber or chambers of the internal combustion engine.

It is also well recognized in the prior art that the sensing metal oxide should be heated to a relatively high temperature in order to exhibit the sensing characteristics. Further, since the electrical resistance of the metal oxide is also sensitive to changes in the temperature, it is recognized that the metal oxide should be maintained at constant temperature when functioning as a sensor for the gas composition as aforesaid. Hence, it is known to use a heater element adjacent the metal oxide sensor element and to use a thermocouple, also adjacent the sensor element in order to measure the temperature and feed this information to a circuit for controlling the heater element thereby to maintain the temperature constant.

THE PROBLEM SOLVED BY THE PRESENT INVENTION

With the availability of all of the relevant prior knowledge, as outlined above, it might be expected to be but a simple matter to construct a device embodying the sensing element and the various other components. In point of fact, there is no great difficulty in constructing such a device as an experimental tool and hence for use under friendly and closely controlled conditions. However, as a practical matter, if such devices are to be used in the exhaust systems of automobiles and other automotive vehicles, then it is imperative that the sensor device not only be relatively simple and inexpensive to manufacture, but that it also be sufficiently rugged to withstand the severe and relatively uncontrolled conditions of mechanical shock and vibration, extremely rapid temperature changes, etc. to which the device is exposed. Hence, the problem has resided in arriving at a structure which meets these stringent demands. The present invention solves this problem.

SUMMARY OF THE INVENTION

Briefly, in accordance with the present invention the aforesaid problem is solved by a sensor device which comprises an electrically insulative ceramic element having bonded on an exposed surface thereof a layer of the oxygen sensing metal oxide, preferably titanium dioxide, a pair of metal leads for the metal oxide sensing element, these metal leads preferably also being bonded onto the surface of the ceramic element; and there being a layer of electrical resistance heating material adjacent to the metal oxide layer but electrically insulated therefrom by a thin layer of the ceramic, a pair of electrical leads for the electrical resistance heating material, and a layer of ceramic covering the electrical resistance heating material. In the preferred embodiment of the invention the ceramic element is of monolithic structure, the electrical resistance heating material being embedded in and surrounded by the ceramic. Further in accordance with the preferred embodiment of the invention, the device also includes a layer of thermistor material, which functions as a heat sensing element, along with electrical leads for the layer of thermistor material, this layer being located in close spaced relationship to the metal oxide sensing element. In its much preferred form, the monolithic ceramic element, with its associated layers and electrical leads as aforesaid, is in the shape of an elongated plate with the metal oxide layer and the embedded electrical resistance heater layer being located closely adjacent one end thereof and with the various electrical leads extending lengthwise of the plate to, or adjacent to, the other end thereof where the leads are exposed for forming the required electrical connections with the control circuitry. Further in accordance with the most preferred embodiment of the invention, this elongated plate is mounted in a hollow metal sleeve by an electrically insulative material, the exterior of the metal sleeve being provided with means, such as a threaded fitting, for securing the device into the exhaust manifold or other pipe or chamber through which the gases to be measured are conducted.

By using as the ceramic for the element a high mechanical strength ceramic, preferably aluminum oxide base ceramic, the monolithic element has ample mechanical strength to withstand the shock and vibration to which it is exposed, and the mounting for the monolithic element within the metal sleeve further augments the mechanical shock resistance. Further, where, as in the preferred embodiment, the element is in the form of a thin plate, this shape of the element increases its resistance to withstand cracking or other deterioration from the rapid changes in temperature to which it is exposed as, for example, an engine start-up or when the heater element is actuated prior to or simultaneously with engine start-up. Still further, and as will be described in detail hereinafter, particularly by reason of the thin plate shape of the monolithic ceramic element with its associated layers and leads, this element and the entire device can be manufactured simply and at low cost.

These and other features and advantages of the invention will appear more clearly from the following detailed description thereof, made with reference to the drawings which will now be identified.

THE DRAWINGS

DETAILED DESCRIPTION OF THE INVENTION

Figure 1:
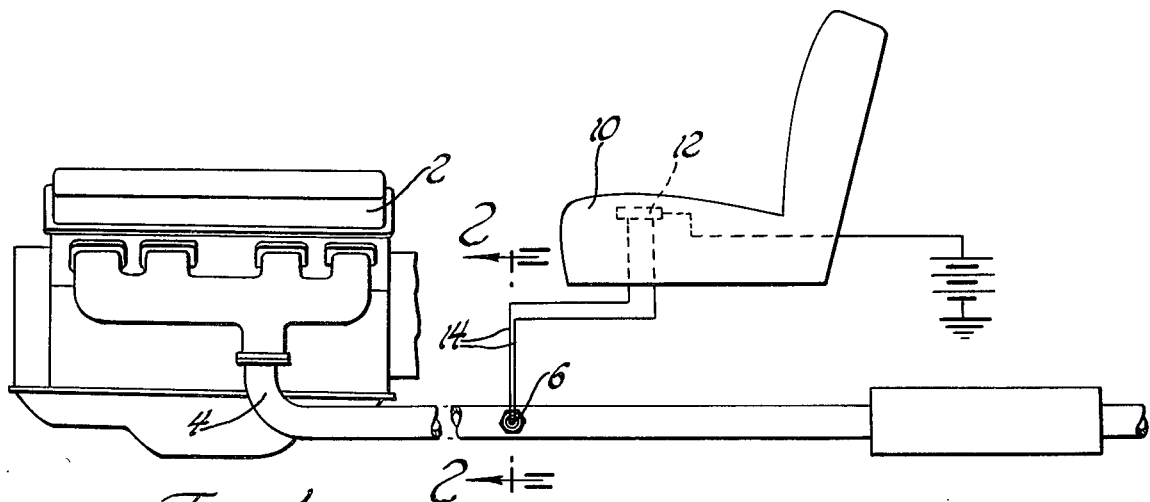
FIG. 1 is a schematic view of an internal combustion engine and its exhaust pipe and shows a typical location for the sensing device of the present invention FIG. 1 also diagrammatically shows the underside of the driver's seat of an automotive vehicle in which the sensing device is mounted, along with switching means positioned underneath the seat and associated with the sensing device.

Referring now to FIG. 1, there is shown a reciprocating type internal combustion engine 2 having an exhaust manifold and exhaust pipe 4. The exhaust pipe is provided with an opening in which there is secured a device 6 which is made in accordance with the present invention and which is for the purpose of determining the composition of the gases flowing through the pipe. In operation, if the sensing device 6 measures too high a concentration of unburned or partially burned hydrocarbons in the exhaust gases, this information is fed in a "feed back system", i.e. it is fed through electrical leads into a control mechanism (not shown) and is transmitted from the control mechanism to suitable mechanical linkage (not shown) for adjusting the air/fuel ratio of the gaseous mixture fed into the combustion chambers of the engine. It will be understood, of course, that the installation and system shown in FIG. 1 is but an example, though a very important one, of one use and one location for the device of this invention; and it will also be understood that except for the device 6, as will hereinafter be described, the system as thus far described immediately above is well known in the art as are the control mechanisms for translating the measurements received from the sensing device into actuations for adjusting the air/fuel ratio of the mixture fed into the combustion chambers of the engine.

FIG. 1 also shows diagrammatically the underside 10 of the driver's seat of the automotive vehicle and switch 12 which is connected by electrical leads 14 to the device 6. The operation of the switch, in association with the device 6, can more appropriately be described hereinafter.

Figure 2:
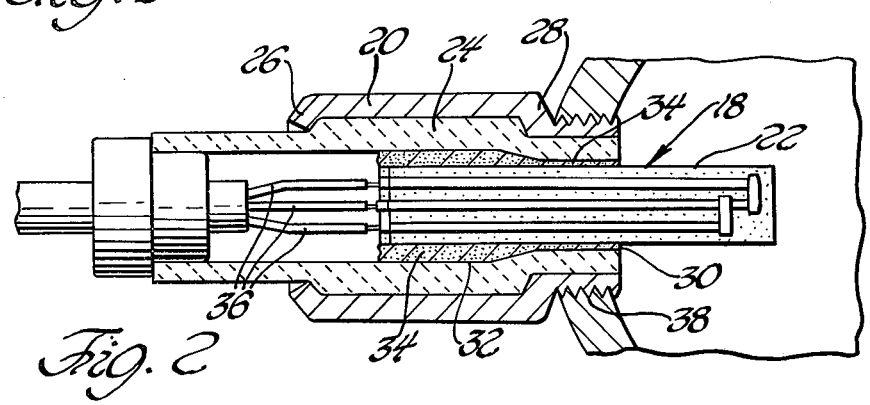
FIG. 2 is a view, in enlarged scale, taken on the line 2—2 of FIG. 1 and showing a device embodying the present invention.

Referring now to FIG. 2, the device 6 comprises a ceramic element 18, preferably of monolithic structure, with its associated layers and leads, as hereinafter described, this ceramic element being in the form of a thin elongated plate. This element 18 is mounted in a cylindrical metal tube 20 in such manner that only the sensing end 22 of the element 18 extends outwardly from the end of the metal tube 20. The means for mounting the element 18 in the metal tube 20 comprises an electrically insulative heat resistant sleeve 24, which can be of sintered alumina or mullite ceramic, held in the metal tube by a pair of shoulders 26 and 28 on the metal tube. One end 30 of the bore of the ceramic sleeve is of rectangular cross-section to accommodate the rectangular cross-section of the sensor element which extends into the bore. The other end 32 of the bore is of round cross-section. A potting compound 34 such as a mixture of magnesium oxide or other ceramic powder and sodium silicate or a conventional phosphate binder, is packed into the bore thereby to support the sensor element in the ceramic sleeve and provide a seal. The sensing end of the sensor element extends outwardly from the end of the ceramic sleeve and lead wires 36, secured to the leads on the sensor element, extend from the other end of the sleeve. A threaded section 38 on the metal tube 20 provides the means for securing the device in the wall of the conduit or chamber containing the gases to be measured.

The function of the mounting, in this preferred embodiment, is to mount the element 18 in such manner as to provide a seal and also to inhibit the transmission of mechanical shock or vibration to the sensor element. In this regard, it is desirable that the dimensioning of the rectangular end of bore 30 be such that there not be a really tight pressured fit between the monolithic element and the sleeve.

Figure 3:
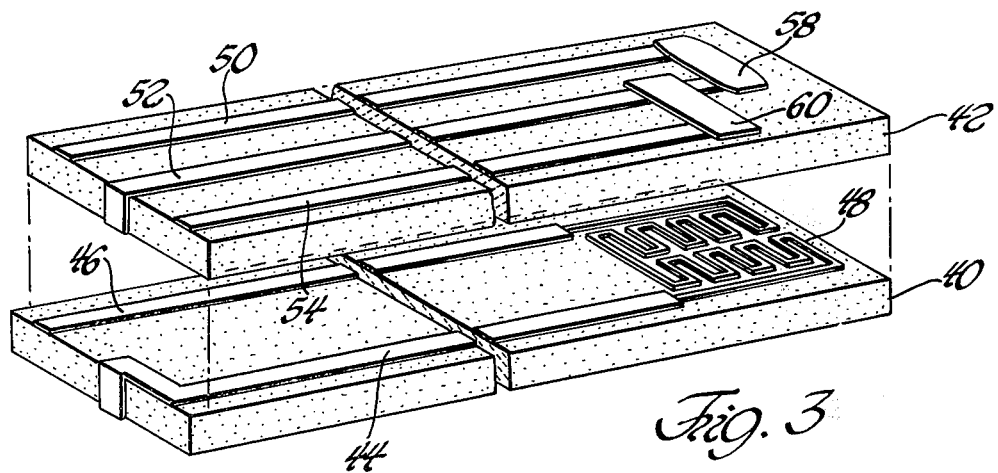
FIG. 3 is a perspective view showing components, at one stage in manufacture, from which is manufactured the sensing element of the device shown in FIG. 2.

The structure of the element 18, and its associated layers and leads, can best be understood by reference to FIG. 3 and a description of the preferred method for manufacture of the monolithic element.

Referring now to FIG. 3, there are shown two strips 40 and 42, of a material of the same formulation and consisting of a ceramic powder formulation bonded by an organic binder. In other words, each of the thin elongated rectangular strips 40 and 42 consists of a mixture of desired ceramic powder formulation and an organic material, generally and preferably a plasticized organic resin, the ceramic ingredients constituting preferably upwards of 90% of the total formulation and hence the organic ingredients preferably being less than 10% by weight of the total formulation. In practice, the ceramic powder formulation is milled in a conventional manner in a ball mill, and this ceramic powder formulation is then mixed with the organic ingredients - generally and preferably a plasticized organic resin as stated - and after a uniform mixture of the organic ingredients and the ceramic ingredients is attained, this mixture is then formed into a thin sheet. This can be accomplished by extrusion of the mixture into the thin sheet or by the addition to the mixture of suitable solvents for the organic material so as to form the mixture into a viscous liquid which viscous liquid can then be poured against a smooth surface thereby to form a sheet of the desired mixture upon evaporation of the solvents. From such a sheet, be it extruded or be it cast against a smooth surface as aforesaid, there can be cut the rectangular strips as shown at 40 and 42. Further as regards the manufacture of sheets from which the strips 40 and 42 can be cut, reference is here made to the article entitled "The Manufacture of Fine- Grained Alumina Substrates for Thin Films" by Daniel J. Shanefield and Richard E. Mistler, Western Electric Engineering Journal, 15 (2) 1971, the teachings of which article are illustrative of the techniques, well known in the art, which can be used.

Referring now to strip 40, there is printed or silk screened thereon, a moly-manganese or other metallizing composition to form leads 44 and 46. Metallizing compositions for the formation of such metal conductive paths on ceramic are well-known in the art. Reference is here made, for example, to U.S. Pat. No. 3,661,595.

Next, there is silk screened or printed onto strip 40 a suitable composition to provide an electrical resistance heating element 48. Platinum is one example. Another example is tungsten. So-called "inks" for the printing of such electrical resistance heating elements onto organic bonded ceramic sheet or strip are already well-known in the art and are commercially available from, for example, E.I. DuPont deNemours of Wilmington, Delaware. Such inks are a mixture of the resistance material, in powder form, organic resin or the like to function as a binder and a suitable organic solvent or solvents.

As illustrated in FIG. 3, it is desirable that the electrical resistance heating material be printed or silk screened onto strip 40 in a pattern which provides a narrow lengthy path, e.g. a zig-zag or back-and-forth narrow path.

Onto strip 42 there is printed or silk screened three metallized leads 50, 52 and 54 which can be of the same composition as that of the leads silk screened or printed onto the strip 40. With the leads 50, 52 and 54 printed or silk screened onto the strip 42, there is next applied to this strip a layer of titanium dioxide, 58, bridging the leads 50 and 52, and a layer of thermistor material 60, bridging the leads 52 and 54. The thermistor material can, for example, be yttria-stabilized zirconium dioxide — typically a mixture of 15 percent yttria and 85 percent zirconia, by weight. Of course the titania and the thermistor material are applied in the form of a powder mixed with liquid vehicle and a small amount of organic binder. The organic binder and vehicle, and the properties thereof, as taught in the aforesaid U.S. Pat. No. 3,661,595 are examples.

At this point it should be noted that strip 40 is longer than strip 42, and lead 52 of strip 42 is carried around and over the bottom edge of the strip so that when strip 40 is placed on strip 42, there is electrical contact between lead 52 of strip 40 and lead 44 of strip 42. This is simply for the purpose of enabling a three electrical lead system rather than four leads.

With strips 40 and 42 prepared and with the layers and leads, as aforesaid, applied thereon, the next step is to superimpose over and bond to strip 40, strip 42 with the layers 58 and 60 being positioned over the heater 48. This can be easily accomplished by applying to the underside of strip 42 a very thin coating of solvent for the organic resin material used as a binder in both strips and then pressing them together, preferably with the application of heat as well as pressure. By this operation, the strips are bonded together and hence the layer of electrical resistance material and its leads are bonded to the back surface of strip 42. After strip 42 is superimposed over and bonded to strip 40, this bonded assembly of the two strips is placed in a kiln and fired to the sintering temperature of the ceramic. In the early stages of this firing operation all the organic material in the strips vaporizes or burns out, and when the sintering temperature is reached, the ceramic material sinters and results in a monolithic ceramic element — the monolithic ceramic element 18. During firing there is shrinkage and hence the dimensions of the strips must be sufficient to provide, after firing, the dimensions desired of the monolithic element. Since shrinkage for any given strip formulation can be easily determined by experiment, it is a simple matter to select the appropriate dimensions for the strips in order to attain the desired size monolithic element.

By using the term "monolithic" in describing the element 18 is meant that the electrically insulative ceramic thereof is of unitary structure. This is because in the sintering which occurs during the firing, the sintered ceramic plates resulting from the two strips 40 and 42 are simultaneously sintered together with the result that there are no longer two separate plates but instead they are so bonded together as to provide a unitary or monolithic structure.

On the exposed face of the monolithic ceramic element there is the thin layer of titanium dioxide 58 bonded to the ceramic, and having the spaced leads 52 and 54 in electrical contact therewith, and there is the adjacent thermistor layer 60 with its spaced leads 50 and 52 in contact therewith, all of the leads extending longitudinally of the monolithic ceramic element to the other end thereof. Embedded in the ceramic monolithic element is the thin layer of electrical resistance heating layer 48 and its associated electrical leads 44 and 46 which, like the exposed leads, extend longitudinally of the monolithic element to the end thereof. The electrical resistance heating layer 48 is adjacent and parallel to the titanium dioxide layer but is separated electrically from the titanium dioxide by a thin layer of the ceramic of the monolith. As has been alluded to previously herein, and as will be descibed further hereinafter, the important function of the electrical resistance heating layer is to very rapidly raise the temperature of the titanium dioxide layer to a predetermined temperature level, and then maintain the titanium dioxide layer at that temperature. In this regard, it is desirable that the thickness of the strip 40 be greater than the thickness of the strip 42, to the end that in the fired structure there is more ceramic behind the electrical resistance heating element than between the electrical resistance heating element and the titanium dioxide layer. By way of such difference in thickness, there is assurance that a higher percentage of the heat output of the electrical resistance heating layer is effective in heating the titanium dioxide layer, the greater thickness of the ceramic behind the electrical resistance heating layer functioning as thermal insulation.

The exposed end portions of the leads can be electroplated or chemically plated with a thin deposit of metal, for example gold, in order to simplify the brazing or soldering thereto of metal lead wires.

It is desirable that the ceramic of the monolith be uniform. That is, it is desirable that the formulation of strip 40 be identical to the formulation of strip 42. Where the compositions are identical, there is minimum problem of warpage during firing by reason of differential in composition and therefore shrinkage during firing.

Suitable ceramics for use as the element 18 are cordierite, beta-spondumene, mullite and alumina, the latter being preferred not only because of its high mechanical strength but also because its coefficient of thermal expansion is close to that of titania. By alumina ceramic I mean ceramic containing upwards of about 85% by weight aluminum oxide and the remainder fluxing or grain growth inhibiting additives. Where the alumina ceramic contains silica, there is an interstitial glassy phase. In the case where no silica is present, any additives present generally function simply as grain growth inhibitors during firing. Examples of alumina base ceramic are offered by U.S. Pat. Nos. 2,272,618 and 3,377,176.

The preferred total thickness for the ceramic plate is about 1/8 inch. It is preferred that the thickness of the ceramic behind the electrical resistance heating element be greater than 1/16 inch, and that the thickness of the layer of ceramic between the electrical resistance heating element and the titanium dioxide layer be less than 1/16 inch. Of course, in translating this back into the thicknesses for the strips 40 and 42, the shrinkage which occurs during firing must be taken into account. It is preferable that the titania layer have a post-firing thickness not exceeding about 1/16 inch and a density of about 80% to 90% of theoretical, i.e. of the theoretical, highest density for titania. The layer of resistance heating material, the thermistor layer and the leads can and preferably should be thinner than the layer of titanium oxide. Whereas it is preferred that the ceramic element be of monolithic structure, the ceramic layer 40 can, if desired, be bonded to ceramic 42 by a glazing material or the like, or can consist of a relatively thick layer of a ceramic coating over the back of ceramic 42.

The electrical resistance heating layer and its leads can be applied and bonded to the back side of ceramic 42 prior to applying the ceramic coating.

In order for the titanium dioxide, which will be in its rutile form, to perform to its optimum advantage as a sensing material, it must be brought to a temperature and maintained at a temperature of at least about 700° C. The function of the electrical resistance heating layer 48 is to very rapidly bring the titanium dioxide layer to a constant temperature at or about 700° C, and maintain the titanium dioxide layer at such constant temperature. It should be noted that at this temperature there is no possibility of formation of carbon on the surface of the titanium dioxide such as would shunt its electrical resistivity. But getting back now to the practical aspects of the operation of the device, it will be obvious that what is desirable is that the titanium dioxide sensing layer be brought to its optimum operating temperature, for sensing, prior to, simultaneously with, or at least as soon as possible after, the time when the engine is started and when the device 6 commences its accurate monitoring of the emissions from the engine, with feedback, as described, to the engine to correct the air/fuel ratio of the mixture fed into the engine, I have provided underneath the driver's seat 10, a switch 12, which is connected by suitable electrical connections 14 to the electrical resistance heating element of the device 6. In other words, the electrical resistance heating element of the device, in this preferred embodiment, does not become actuated just when the engine is started, but instead is actuated when the driver of the automotive vehicle sits in the driver's seat thereby actuating the switch 12 which, in turn, causes flow of current from the battery to the electrical resistance heating element and hence brings the titanium dioxide layer up to its optimum sensing temperature prior to, at, or at least as soon as possible after, engine start-up.

Figure 4:
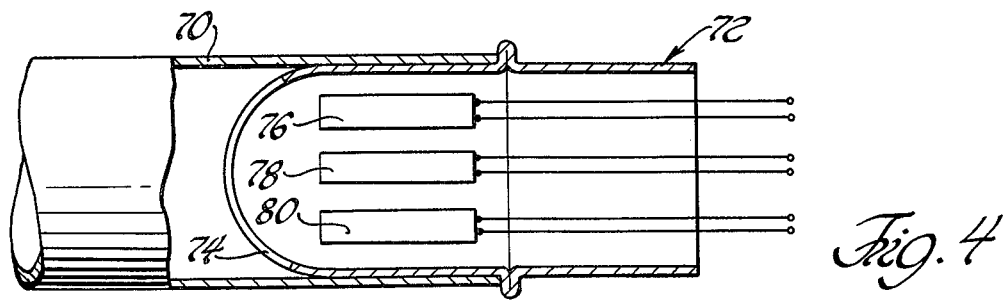
FIG. 4 is a view showing in cross-section the end of the exhaust stack of an automobile having a catalytic converter in its exhaust system, and showing a device inserted into the exhaust stack for the purpose of analyzing the gases emanating therefrom to determine the level of catalytic activity of the catalyst in the catalytic converter.

I now refer to FIG. 4. In this figure, 70 is the end of the exhaust stack of an automotive vehicle having a hydrocarbon burning engine and fitted with a catalytic converter to convert to carbon dioxide and water unburned or partially burned hydrocarbons emanating from the engine. In this FIG. 4, 72 is a device for measuring the level of catalytic activity of the catalyst in the catalytic converter. In operation, the gases from the exhaust stack flow through the screen or grid 74, and outwardly therefrom, after having passes against the probes 76, 78 and 80. Probe 76 is a temperature measuring probe — for example, a thermocouple; 78 is a temperature measuring probe, for example a thermocouple, but with a coating of, or surrounded by, a catalyst, such as platinum, for catalyzing the burning of partially burned or unburned hydrocarbons. Probe 80 is an oxygen sensing instrument which can be identical to that described in the aforesaid — with titanium dioxide or other oxygen-sensitive metal oxide as the sensing element. In operation, when the exhaust gases from the exhaust stack circulate against the three probes, probe 76 simply registers the temperature of the exhaust gases and probe 78, with its associated catalyst, registers a temperature which is a function of the amount of unburned or partially burned hydrocarbons in the exhaust gases. If there is a temperature differential between probes 76 and 78, then it means that the catalytic converter is not performing its intended function of totally burning all unburned or partially burned hydrocarbons to carbon dioxide and water. There could be two reasons why, in the case of a temperature differential between probes 76 and 78, the catalytic converter is not performing its intended function. One reason would be that the catalyst in the catalytic converter is dead. The other reason would be that the catalytic converter is not being served with sufficient oxygen to perform its function. Probe 80, the oxygen-sensing probe, provides the key information to determine, in the case of a differential between the temperature registered by probes 76 and 78, whether the cause is oxygen deficiency or whether the catalyst is dead. If the cause is oxygen deficiency, as would be indicated by probe 80 given a reading that there is no oxygen whatsoever in the exhaust gases, then it becomes a matter of attending to greater feed of oxygen to the converter until the probe 80 does register the pressure of oxygen in the exhaust gases. Then, if there continues to be a significant difference between the readings from probes 76 and 78, this means that the catalyst of the converter is inoperative and requires replacement.

It will be understood that whereas the invention has been described in its particulars with reference to various preferred embodiments thereof, changes and modifications may be made all within the full and intended scope of the claims which follow.

The embodiments of the invention in which an exclusive property or privilege is claimed are defined as follows:

1. An oxygen sensing device particularly suited as a sensor for the exhaust gases of an internal combustion engine, said sensing device comprising an electrically insulative ceramic element having bonded on a surface thereof a layer of an oxygen sensing metal oxide, electrical leads for the oxygen sensing metal oxide, a thin layer of electrical resistance heating material adjacent the layer of oxygen sensing metal oxide but separated from said layer of oxygen sensing metal oxide by a layer of the electrical insulative ceramic, electrical leads for the electrical resistance heating material, and a layer of ceramic covering the layer of electrical resistance material, said device also including a layer of thermistor material bonded to a surface of said ceramic element adjacent said layer of oxygen sensing metal oxide and electrical leads for said thermistor material.

2. An oxygen sensing device as set forth in claim 1 wherein said electrically insulative ceramic element is in the form of a plate.

3. An oxygen sensing device as set forth in claim 2 wherein said layer of ceramic is monolithic with said ceramic element.

4. An oxygen sensing device as set forth in claim 3 wherein said ceramic element has a thickness less than that of said layer of ceramic.

5. An oxygen sensing device as set forth in claim 4 wherein the thickness of said element is less than about 1/16 inch, the thickness of said layer of ceramic is greater than about 1/16 inch.

6. An oxygen sensing device as set forth in claim 5 wherein said layer of oxygen sensing metal oxide is titanium oxide, has a thickness not greater than about 1/16 inch and a density of from about 80% to 90% of the theoretical highest density for titanium oxide.

7. An oxygen sensing device as set forth in claim 6 wherein said device also includes a temperature sensing element to measure the temperature of the layer of oxygen sensing metal oxide.

8. An oxygen sensing device as set forth in claim 7 wherein said temperature sensing element is a layer of thermistor material.

9. An oxygen sensing device as set forth in claim 8 wherein said ceramic element and said layer of ceramic are aluminum oxide ceramic.

10. An oxygen sensing device as set forth in claim 1 wherein said layer of oxygen sensing metal oxide is titanium oxide and wherein said ceramic element is aluminum oxide ceramic.

11. An oxygen sensing device as set forth in claim 1 wherein said layer of ceramic is monolithic with said ceramic element.

12. An oxygen sensing device as set forth in claim 1 wherein said device also includes a temperature sensing element to measure the temperature of said layer of oxygen sensing metal oxide.

13. An oxygen sensing device as set forth in claim 1 wherein said ceramic element is in the form of an elongated plate, said layers of oxygen sensing metal oxide and electrical resistance heating material being adjacent one end of said elongated plate and the electrical leads extending toward the other end of said elongated plate.

14. An oxygen sensing device as set forth in claim 13 wherein said layer of ceramic is monolithic with said ceramic element.

15. An oxygen sensing device as set forth in claim 13 wherein said other end of said elongated plate is mounted in a body of electrically insulative material.

16. An oxygen sensing device as set forth in claim 15 wherein said body of electrically insulative material is secured within a metal tube, said metal tube having means thereon for mounting said device.

17. An oxygen sensing device as set forth in claim 13 wherein said device also includes a layer of thermistor material bonded to said ceramic element adjacent said layer of oxygen sensing metal oxide for measuring the temperature of said layer of oxygen sensing metal oxide.

18. An oxygen sensing device as set forth in claim 13 wherein each of said pair of leads for said layer of oxygen sensing metal oxide comprises a thin elongated layer of metal bonded to the surface of said ceramic element.

19. An oxygen sensing device as set forth in claim 1 wherein said ceramic element is in the form of a plate, wherein said layer of ceramic is also in the form of a plate, said second mentioned plate being bonded to said first mentioned plate, and wherein said layer of electrical resistance heating material is bonded to said second mentioned plate, each of the electrical leads for said layer of electrical resistance heating material comprising a thin elongated layer of metal bonded to said second mentioned plate.

20. An oxygen sensing device as set forth in claim 19 wherein said plates are bonded together so as to form a monolithic structure.

* * * * *